US012048763B2

(12) United States Patent
Yellepeddi et al.

(10) Patent No.: US 12,048,763 B2
(45) Date of Patent: Jul. 30, 2024

(54) COMPOSITIONS AND METHODS FOR TREATING SIALORRHEA

(71) Applicant: University of Utah Research Foundation, Salt Lake City, UT (US)

(72) Inventors: Venkata K. Yellepeddi, Salt Lake City, UT (US); Nancy Alice Murphy, Salt Lake City, UT (US); Hamidreza S. Ghandehari, Salt Lake City, UT (US); Harlan R. Muntz, Salt Lake City, UT (US); Bhuvanesh Kumar Yathavan, Salt Lake City, UT (US); Kevin Watt, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 18/051,283

(22) Filed: Oct. 31, 2022

(65) Prior Publication Data
US 2023/0149306 A1    May 18, 2023

Related U.S. Application Data

(60) Provisional application No. 63/274,350, filed on Nov. 1, 2021.

(51) Int. Cl.
*A61K 9/06* (2006.01)
*A61K 9/00* (2006.01)
*A61K 31/46* (2006.01)
*A61K 47/32* (2006.01)
*A61P 43/00* (2006.01)

(52) U.S. Cl.
CPC ............... *A61K 9/06* (2013.01); *A61K 9/006* (2013.01); *A61K 31/46* (2013.01); *A61K 47/32* (2013.01); *A61P 43/00* (2018.01)

(58) Field of Classification Search
CPC .......... A61K 9/006; A61K 9/06; A61K 47/32; A61K 31/46; A61P 43/00
See application file for complete search history.

(56) References Cited

U.S. PATENT DOCUMENTS

| | | | | |
|---|---|---|---|---|
| 9,198,897 | B2 * | 12/2015 | Merello | ............ A61K 9/0056 |
| 9,433,616 | B2 | 9/2016 | Merello et al. | |
| 2018/0235869 | A1 | 8/2018 | Bodor | |
| 2018/0250265 | A1 | 9/2018 | Bodor | |
| 2019/0117605 | A1 | 4/2019 | Heller et al. | |
| 2019/0365689 | A1 | 12/2019 | Kelley, III et al. | |

OTHER PUBLICATIONS

Murrin KR. A study of oral atropine in healthy adult subjects. Br J Anaesth. May 1973;45(5):475-480. doi: 10.1093/bja/45.5.475. PMID: 4715595. (Year: 1973).*

Thota Ganesh, et al. Inhibition of pilocarpine-induced fluid secretion by ethylatropine bromide. Abstract. 253rd National Meeting ( 2017) Mar. 30-Apr. 7, 2017 American Chemical Society. pp. 1-2 (Year: 2017).*

Alcon (2018). Viscotears® Liquid Gel [carbomer (polyacrylic acid)]—Patient Information Leaflet.

Allison RR, et al. 2014. "Multi-institutional, randomized, double-blind, placebo-controlled trial to assess the efficacy of a mucoadhesive hydrogel (MuGard) in mitigating oral mucositis symptoms in patients being treated with chemoradiation therapy for cancers of the head and neck." Cancer, 120(9):1433-1440.

Da Silva et al., "Assessing Mucoadhesion in Polymer Gels: The Effect of Method Type and Instrument Variables." 10:254-273, 2018.

De Simone GG, et al. 2006. "Atropine drops for drooling: a randomized controlled trial." Palliat Med, 20(7):665-671.

Drisanna W, et al. "Prediction of plasma and salivary pharmacokinetics of atropine in pediatric sialorrhea patients using a PBPK modeling approach." 2019 SACNAS—The National Diversity in STEM Conference, Honolulu, HI.

Fini A, et al. (2011). "Mucoadhesive gels designed for the controlled release of chlorhexidine in the oral cavity." Pharmaceutics 3: 665-79.

Keegan G, et al. 2007. "An in vitro assessment of bioadhesive zinc/carbomer complexes for antimicrobial therapy within the oral cavity." Int J Pharm, 340(1-2):92-96.

Kelly HM, et al. 2004. "Bioadhesive, rheological, lubricant and other aspects of an oral gel formulation intended for the treatment of xerostomia." Int J Pharm 278(2):391-406.

Lawrence R and Bateman N. 2018. "Surgical Management of the Drooling Child." Curr Otorhinolaryngol Rep, 6(1):99-106.

Leung JG and Schak KM. 2017. "Artificial salivas for in vitro studies of dental materials." Schizophr Res 185:202-203.

Morgante, et al. "The burden of sialorrhea in chronic neurological conditions: current treatment options and the role of incobotulinumtoxin A. (Xeomin®)". Ther Adv Neurol Disord 12:1-21, 2019.

Navazesh M, et al. (2008). "Measuring salivary flow: challenges and opportunities." J Am Dent Assoc 139 Suppl: 35S-40S.

Norderyd J, et al. 2017. "Sublingual administration of atropine eyedrops in children with excessive drooling—a pilot study." Int J Paediatr Dent, 27(1):22-29.

Parkes J, e al. "Oromotor dysfunction and communication impairments in children with cerebral palsy: a register study." Dev Med Child Neurol, 52(12):1113-1119 (2010).

Protus BM, et al. 2013. "Evaluation of atropine 1% ophthalmic solution administered sublingually for the management of terminal respiratory secretions." Am J Hosp Palliat Care, 30(4):388-392.

Reid SM, et al. (2010). "The Drooling Impact Scale: a measure of the impact of drooling in children with developmental disabilities." Dev Med Child Neurol 52: e23-8.

Reid SM, et al. "Prevalence and predictors of drooling in 7- to 14-year-old children with cerebral palsy: a population study." Dev Med Child Neurol, 54(11):1032-10363 (2012).

Reid SM, e al. "Long-term impact of saliva control surgery in children with disability." J Plast Reconstr Aesthet Surg, 72(7):1193-1197 (2019).

(Continued)

*Primary Examiner* — Noble E Jarrell
*Assistant Examiner* — Richard Grant Peckham
(74) *Attorney, Agent, or Firm* — BALLARD SPAHR LLP

(57) ABSTRACT

Disclosed herein are methods and compositions comprising atropine and a polymer in a gel formulation for decreasing saliva production and treating sialorrhea.

16 Claims, 6 Drawing Sheets

(56) References Cited

OTHER PUBLICATIONS

Reid SM, et al. 2019. "Anticholinergic medications for reducing drooling in children with developmental disability." Dev Med Child Neurol 62(3):346-353.

Saarnivaara L, et al.(1985). "Comparison of pharmacokinetic and pharmacodynamics parameters following oral or intramuscular atropine in children. Atropine overdose in two small children." Acta Anaesthesiol Scand 29: 529-36.

Shaikh et al., "Mucoadhesive drug delivery systems." J. Pharm Bio Allied Sci. 3:89-100, 2011.

Silva et al., "Mucoadhesive Oral films: The potential for unmet needs." International Journal of Pharmaceutics. 494:537-551, 2015.

Singla AK, et al. 2000. "Potential applications of carbomer in oral mucoadhesive controlled drug delivery system: a review." Drug Dev Ind Pharm, 26(9):913-924.

Speyer R, et al. "Prevalence of drooling, swallowing, and feeding problems in cerebral palsy across the lifespan: a systematic review and meta-analyses." Dev Med Child Neurol 61(11):1249-1258 (2019).

Van Der Poorten and De Hert. (2019). "The sublingual use of atropine in the treatment of clozapine-induced sialorrhea: A systematic review." Clin. Case Rep. 7:2108-2113.

Yellepeddi, V, et al. "The effectiveness of atropine for the treatment of excessive salivation." PROSPERO, 2019, CRD42019126789.

* cited by examiner

COMPOSITIONS AND METHODS FOR TREATING SIALORRHEA

CROSS REFERENCE TO RELATED APPLICATIONS

This application claims the benefit of U.S. Provisional Application No. 63/274,350, filed Nov. 1, 2021. The content of this earlier filed application is hereby incorporated by reference herein in their entirety.

BACKGROUND

Sialorrhea is excessive salivation and is a significant quality of life issue in children with neurodevelopmental disorders such as cerebral palsy and dystonia. Adverse physical consequences of sialorrhea include perioral skin excoriation and infection as well as the associated psychosocial stigma due to humiliation and social withdrawal. Current pharmacological treatment for sialorrhea includes off-label use of adult formulations of anticholinergic agents, and are associated with significant side effects due to systemic absorption, risk of medication errors, and poor compliance.

SUMMARY

Disclosed herein are stable gel formulations comprising atropine for intra-oral administration of the atropine to a subject in an amount effective for decreasing saliva production in the subject.

Disclosed herein are methods of reducing the accumulation of saliva from the mouth of a subject, the methods comprising applying intraorally a stable gel formulation of atropine in a pharmaceutically acceptable carrier to the subject.

Disclosed herein are methods of treating sialorrhea in a subject, the methods comprising applying intraorally a stable gel formulation of atropine in a pharmaceutically acceptable carrier to the subject.

Other features and advantages of the present compositions and methods are illustrated in the description below, the drawings, and the claims.

BRIEF DESCRIPTION OF THE DRAWINGS

FIG. 1A shows a representative chromatogram of atropine (200 μg/mL). FIG. 1B shows a linearity curve of atropine 25 to 300 μg/mL.

DETAILED DESCRIPTION

Figure 1A:
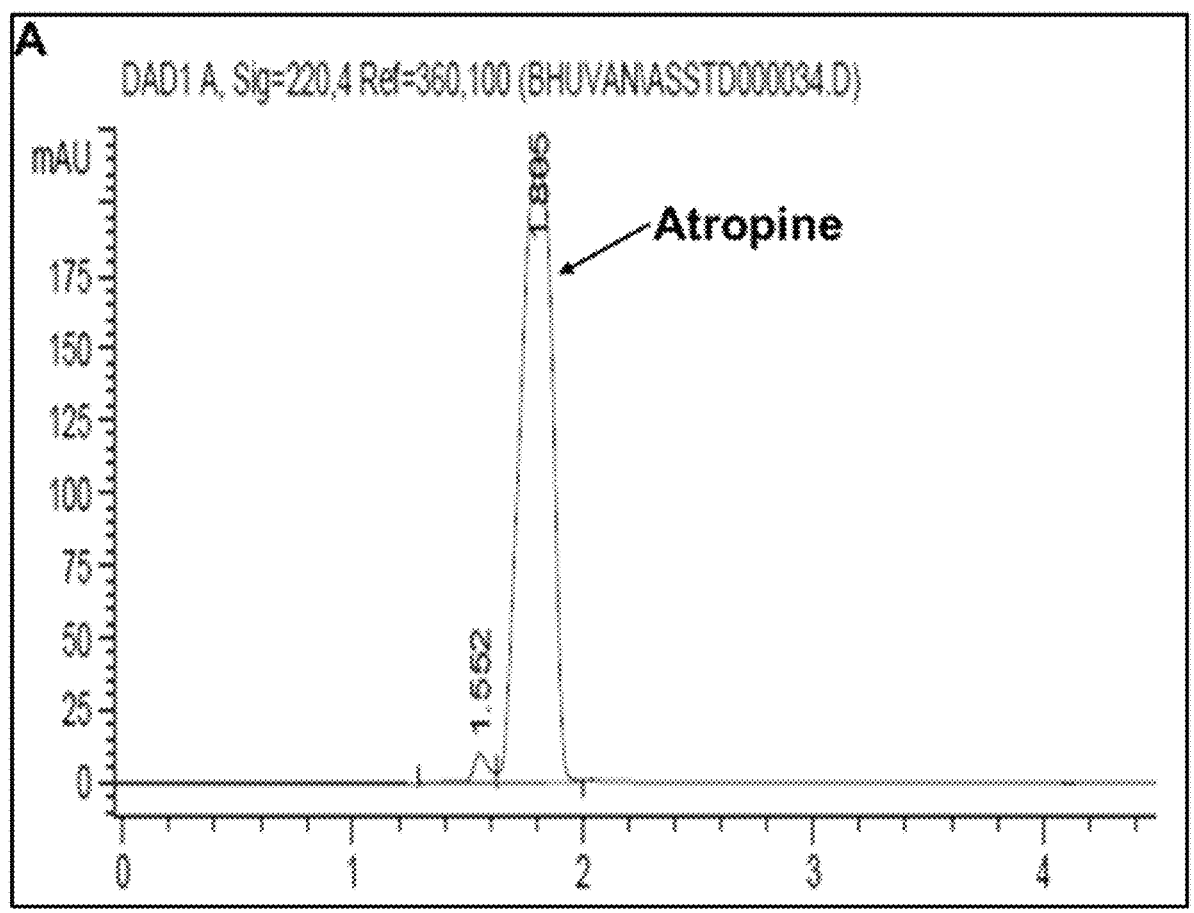
FIGS. 1A-B show the results of a high-performance liquid chromatography method for quantification of atropine in the gel formulation.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or 'approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject is a mammal. In some aspects, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition. The term "patient" includes human and veterinary subjects. In some aspects of the disclosed methods, the "patient" has been diagnosed with a need for treatment for preventing or treating sialorrhea, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be sialorrhea.

As used herein, the terms "intra-oral" "intraorally", and "intra-orally" refer to a route of administration in the area of the mouth, specifically the mouth cavity and mucosal epithelium, without extending to the rest of the alimentary canal. The compositions described herein can be formulated for "intra-oral" administration. "Intra-oral" can also encompass "buccal" administration wherein the disclosed compositions can be placed on the cheek tissue of the oral cavity, "lingual" administration wherein the disclosed compositions can be placed on the tongue, and "sub-lingual" wherein the compositions disclosed herein can be placed under the tongue.

Sialorrhea is the accumulation of saliva and the unintentional loss of the saliva from the mouth, resulting in drooling (Morgante et al., Ther Adv Neurol Disord 12:1-21, 2019). Sialorrhea is due to excessive saliva production by the salivary glands or inadequate saliva removal due to swallowing difficulties. Sialorrhea or drooling is excessive salivation and is a significant quality of life issue in children with neurodevelopmental disorders such as cerebral palsy (CP) and dystonia (Reid S M, e al. 2019. J Plast Reconstr Aesthet Surg, 72(7):1193-1197; and Speyer R, et al. 2019. Dev Med Child Neurol 61(11):1249-1258). Adverse physical consequences of sialorrhea include perioral skin excoriation and infection, and there are psychosocial stigmata related to hygiene, cosmesis and social isolation. Despite drooling being a common problem in disability, affecting approximately 22% to 40% of children with CP (Parkes J, e al. 2010. Dev Med Child Neurol, 52(12):1113-1119; and Reid S M, et al. 2012. Dev Med Child Neurol, 54(11):1032-10363) none of the available treatment options are totally satisfactory (Reid S M, et al. 2019. J Plast Reconstr Aesthet Surg, 72(7):1193-1197).

The term "sialorrhea" is commonly referred to as an "excess production of saliva, or increased retention of saliva in the mouth" or "saliva beyond the lip", which generally presents as "drooling" by a subject. In some aspects, accordingly, a subject who suffers from sialorrhea is unable to properly swallow or expel saliva that accumulates in the mouth so that drooling occurs. In some aspects, the inability to attend to saliva production can be due to one or more impaired functions, including but not limited to impaired swallowing reflex, poor head posture, abnormal structure of the oral cavity, or inadequate oropharyngeal motor function. In some aspects, subjects with sialorrhea may produce lower than normal amounts of saliva. Thus, in the case of sialorrhea, whatever the actual level of saliva production is in a subject, the amount of saliva can be too great for the subject to control without drooling.

Sialorrhea is a frequent symptom of neurological diseases or injuries such as Parkinson's disease, cerebral palsy, motor neuron disease, acquired brain injury and stroke. In these situations, the neural control and coordination of muscles involved in swallowing may be compromised. Thus, drooling may be present in up to 60% of patients with Parkinson's disease and up to 44% of children with cerebral palsy (Speyer et al., Dev. Med. Child Neurol. 61:1249-1258, 2019). Sialorrhea may also occur as the result of drugs used for other indications such as the treatment of schizophrenia with clozapine (Van der Poorten and De Hert. (2019). Clin. Case Rep. 7:2108-2113).

Physical therapists, including speech and language therapists, may assist patients with their symptoms (Morgante et al., Ther Adv Neurol Disord 12:1-21, 2019). Additionally, other treatments include surgery or radiation therapy of the salivary glands. Pharmacological treatments are also widely used to treat sialorrhea, and involves the use of anticholinergic agents (Reid S M, et al. 2020. Dev Med Child Neurol 62(3):346-353). The most commonly used anticholinergic agents are atropine, scopolamine, and glycopyrrolate (Cuvposa®). Cuvposa® (glycopyrrolate oral solution) is approved by the FDA for the treatment of sialorrhea in pediatric patients with neurologic disorders. Anticholinergic drugs, including atropine, hyoscine, glycopyrronium bromide, benzatropine and tropicamide, inhibit the action of the neurotransmitter acetylcholine at the acetylcholine receptors in the salivary glands, thereby reducing saliva production. While these drugs have shown success, several anticholinergic drugs often must be dispensed using an oral syringe into a patient's mouth several times a day. As a result, a significant fraction of the drug may not reach the desired target and, thereby resulting in undesirable systemic effects. Other anticholinergic drugs require the injection. However, sublingual administration of atropine eye drops is the most common off-label treatment for sialorrhea across many institutions in the United States because of low-cost and easy availability (Norderyd J, et al. 2017. Int J Paediatr Dent, 27(1):22-29; Protus B M, et al. 2013. Am J Hosp Palliat Care, 30(4):388-392; and De Simone G G, e al. 2006. Palliat Med, 20(7):665-671). If pharmacological treatment fails, surgical interventions such as salivary duct ligation and gland excision are performed (Lawrence R and Bateman N.

2018. Curr Otorhinolaryngol Rep, 6(1):99-106). Thus, a need exists for a product that reduces the symptoms of sialorrhea without significant systemic effects, that is easy to administer, requires less frequent administration, and provides consistent dosing.

As mentioned herein, the current treatment strategies for the management of sialorrhea include either surgical or pharmacological interventions, or both. The surgical interventions include invasive techniques such as salivary duct ligation, salivary duct relocation, and salivary gland excision. These surgical procedures are expensive and need involvement from multidisciplinary teams. The pharmacological treatment includes administration of oral, local, and systemic anticholinergic drugs such as glycopyrrolate, benztropine, scopolamine and local injections of botulinum toxin.

Despite its FDA approval, Cuvposa® has significant demerits as it is administered systemically and associated with numerous systemic side effects. It is reported that 77% of the carers of children reported at least one adverse effect when their children were treated with Cuvposa® (glycopyrrolate) oral solution (Reid S M, et al. 2020. Dev Med Child Neurol 62(3):346-353). The adverse effects reported included constipation, poor sleep, seizures, and urinary retention. Furthermore, due to these adverse effects, 45% of participants were no longer taking glycopyrrolate by 6 months (Reid S M, et al. 2020. Dev Med Child Neurol 62(3):346-353). Therefore, it is evident that Cuvposa® is not a preferred choice due to its systemic adverse effects after enteral administration of the drug.

Despite their reported effectiveness of some of the current pharmacological treatments, side effects including vomiting, diarrhea, irritability, mood changes and insomnia do occur. To avoid systemic adverse effects, physicians have resorted to topical administration of atropine eye drops onto the oral mucosa. However, due to lack of retention in the targeted site of action, atropine eye drops have to be administered 6-8 times daily, increasing the risk for systemic side effects such as tachycardia, fever, tremors, and restlessness. Frequent administration is required due to the short oral residence time. Furthermore, the use of ophthalmic atropine for sublingual and buccal mucosa administration is not standardized and can result in potential medication errors due to inappropriate administration in the eyes (Leung J G and Schak K M. 2017. Schizophr Res 185:202-203). Moreover, none of the currently available pharmacological agents are specifically approved for the treatment of sialorrhea and are used off-label. The disadvantages of off-label use include: no dosing guidelines for the use of atropine for the treatment of sialorrhea; no consistency amongst clinicians for the treatment strategy leading to unwanted systemic side effects; and a high incidence of medication errors as off-label use involves the use of atropine eye drops delivered sublingually.

A significant unmet need to develop safe and effective treatment options for sialorrhea in pediatric patients with neurodevelopmental disorders exists. Moreover, there is no established atropine dosing regimen for the treatment of sialorrhea that can guide providers in prescribing for individual patients. The development of a stable gel formulation comprising atropine for intra-oral administration of the atropine for sialorrhea addresses an unmet clinical need. As described herein, the mucoadhesiveness of polymers can further be used to increase oral residence time while limiting systemic absorption through the oral mucosa.

Disclosed herein are compositions comprising a stable gel formulation comprising atropine for intra-oral administration of the atropine. In some aspects, these compositions can solve the problems associated with the off-label use of medications for the treatment of sialorrhea. Specifically, the compositions described herein can reduce the frequency of administration, reduce medication errors, limit systemic absorption and decrease systemic side effects. The stable gel formulation comprising atropine for intra-oral administration of the atropine can be prepared with an FDA approved polymer (e.g., carbopol) and contains atropine as an active ingredient. The currently available pharmacological agents currently used are delivered in a solution form. No stable gel formulations of pharmacological agents are currently available or currently used for the treatment of sialorrhea.

The compositions disclosed herein can provide the following advantages over existing solutions: because of its mucoadhesive property, the stable gel formulations described herein can have an increased residence time in the oral cavity and can be administered fewer times; minimal systemic side effects because the anticholinergic agent atropine in the has a greater affinity to the polymer when compared to saliva; improved patient/caregiver compliance because the gel formation is easy to apply in the oral cavity; and the gel formulation can allow application of prespecified dose of atropine to the patient.

Disclosed herein are compositions and methods for use in any situation where it is desirable to decrease the amount of saliva produced by the salivary glands in the mouth of a subject. The compositions and methods described herein can decrease or reduce saliva production for a limited duration, such that the subject in need of treatment thereof or the subject with sialorrhea does not permanently lose the benefit of saliva production for eating, speaking, and general oral and dental health.

Compositions

Disclosed are compositions comprising a stable gel formulation comprising atropine for intra-oral administration of the atropine to a subject in an amount effective for decreasing saliva production in the subject.

Disclosed herein are compositions comprising atropine and Carbopol® 974 NF. In some aspects, the composition can be in the form of a gel.

Disclosed herein are stable gel formulations. In some aspects, the stable gel formulation can comprise atropine. In some aspects, the stable gel formulation can comprise atropine for intra-oral administration of the atropine to a subject in an amount effective for decreasing saliva production in the subject.

In some aspects, the atropine can be atropine sulfate monohydrate. In some aspects, the atropine can be atropine sulfate. In some aspects, the atropine can be any salt form of atropine. In some aspects, the salt can be a pharmaceutically acceptable salt thereof. In some aspects, the atropine can be atropine sulfate anhydrous, atropine hydrochloride, atropine oxide, atropine oxide hydrochloride, atropine methylbromide, atropine borate, atropine nitrate, atropine tartrate, atropine citrate, atropine acetate, or atropine formate.

In some aspects, the atropine can be present in an amount up to about 0.01% to 1% by weight. In some aspects, the atropine can be present in an amount of 0.01%, 0.02%, 0.03%, 0.04%, 0.05%, 0.06%, 0.07%, 0.08%, 0.09%, 0.1% by weight or any amount in between.

In some aspects, the stable gel formulation can further comprise a polymer. In some aspects, the polymer can be a carbomer polymer. In some aspects, the carbomer polymer can be a carbomer 974P polymer. In some aspects, the carbomer 974P polymer can be present in amount up to about 0.5 to 5% by weight. In some aspects, the carbomer polymer can be present in amount up to about 0.5 to 5% by weight. In some aspects, the carbomer polymer can be present in amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between. In some aspects, the carbomer 974P polymer can be present in amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between. In some aspects, the carbomer polymer or carbomer 974P polymer can be any commercially available carbomer polymer or carbomer 974P polymer.

In some aspects, wherein the atropine can be present in amount up to about 0.1% by weight and the carbomer 974P polymer can be present in an amount up to about 5% by weight. In some aspects, the atropine can be present in amount of about 0.01%, 0.02%, 0.03%, 0.04%, 0.05%, 0.06%, 0.07%, 0.08%, 0.09%, 0.1% by weight or any amount in between and the carbomer 974P polymer can be present in an amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between.

In some aspects, the intra-orally administrable, compositions and stable gel formulations described herein can comprise atropine, or pharmaceutically acceptable salt thereof, per one dose in an amount ranging from 0.1 to 10 mg. In some aspects, the atropine, or pharmaceutically acceptable salt thereof can be present in the composition or stable gel formulation in amount of about 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, mg or any amount in between. In some aspects, the atropine, or pharmaceutically acceptable salt thereof can be present in the composition or stable gel formulation in a concentration range of between 25 to 300 µg/mL. In some aspects, the atropine, or pharmaceutically acceptable salt thereof can be present in the composition or stable gel formulation in a concentration range of 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 µg/mL or any amount in between.

In some aspects, the stable gel formulations disclosed herein can have a dissolution rate of 1 to 6 hours. In some aspects, the stable gel formulations disclosed herein can have a dissolution rate of 30 minutes, 1 hour, 1.5 hours, 2, hours, 2.5 hours, 3 hours, 3.5 hours, 4 hours, 4.5 hours, 5 hours, 5.5 hours, 6 hours or any amount of time in between. In some aspects, the stable gel formulations disclosed herein can have a dissolution rate of 1, 2, 3, 4, 5, 10, 15, 20, 25, 30 minutes or any amount of time in between. In some aspects, the stable gel formulations disclosed herein can have a dissolution rate of 30, 35, 40, 45, 50, 55, 60 minutes or any amount of time in between.

In some aspects, flavoring agents (flavors, flavorings) can be used in the compositions or stable gel formulations disclosed herein. In some aspects, the flavors can be selected based on their inability to increase the salivatory response and/or to mask the taste of the atropine. Examples of flavorings that can be used include but are not limited to synthetic flavor oils, flavoring aromatics, oleo resins, and extracts derived from plants, leaves, flowers, and fruits. Examples of flavor oils include, without limitation, spearmint oil, cinnamon oil, peppermint oil, clove oil, bay oil, thyme oil, cedar leaf oil, oil of nutmeg, oil of sage, and oil of bitter almonds. In some aspects, fruit flavors can be used. Examples of fruit flavors include but are not limited to vanilla, chocolate, coffee, cocoa, and various citrus oils, such as lemon, orange, grape, lime, and grapefruit. In some aspects, fruit essences can be used including but not limited to apple, pear, peach, strawberry, raspberry, cherry, plum, pineapple, apricot, and the like. Any of the flavoring agents can also be used individually or in combination. Other flavoring agents that can be used in the compositions or stable gel formulations described herein include but are not limited to aldehydes and esters, for example, cinnamyl acetate, cinnamaldehyde, citral, diethylacetal, dihydrocarvyl acetate, eugenyl formate, p-methylanisole, and the like. Further examples of aldehyde flavorings include, but are not limited to, acetaldehyde (apple); benzaldehyde (cherry, almond); cinnamic aldehyde (cinnamon); citral, e.g., alpha citral (lemon, lime); neral, i.e., beta citral (lemon, lime); decanal (orange, lemon); ethyl vanillin (vanilla, cream); heliotropine, e.g., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, e.g., trans-2 (berry fruits); tolyl aldehyde (cherry, almond); veratraldehyde (vanilla); 2,6-dimethyl-5-heptenal, e.g., melonal (melon); 2-6-dimethyl-octanal (green fruit); and 2-dodecenal (citrus, mandarin); cherry; grape; and combinations thereof. Generally, any flavoring or food additive, such as those described in Chemicals Used in Food Processing, publication 1274 by the National Academy of Sciences, pages 63-258, can be used. The effect of flavors can be enhanced using flavor enhancers such as tartaric acid, citric acid, vanillin, higher alcohols (see, e.g., U.S. Patent Application Publication No. US2004/0022743 A1, published Feb. 5, 2004), and the like. The amount of flavoring employed is normally a matter of preference and subject to such factors as flavor type, individual flavor, and strength desired. Thus, the amount may be varied in order to obtain the result desired in the final composition. Such variations are within the capabilities of those skilled in the art.

In some aspects, non-cariogenic sweeteners can be used in the compositions or stable gel formulations disclosed herein. Examples of the non-cariogenic sweeteners include but are not limited to xylitol, erythritol, sorbitol, mannitol, and maltitol.

Breath freshening agents can also be useful in the compositions or stable gel formulations disclosed herein and include menthol and other flavors or fragrances commonly used for oral hygiene or oral cleansing and include various quaternary ammonium bases.

In some aspects, the compositions and stable gel formulations disclosed herein can also contain one or more coloring agents (colors, colorants). These colorants are known in art as "FD&C" dyes and lakes. The materials acceptable for the foregoing spectrum of use are generally water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene] 1-N-ethyl-N-p-sulfonium benzyl)-2,5-cyclo-hexadienimine]. A full recitation of the FD&C and D&C dyes and their corresponding chemical structures can be found in the Kirk-Othmer Encyclopedia of Chemical Technology, Volume 5, pages 857-884 (Wiley-Interscience, 2005), incorporated herein by reference.

In some aspects, the compositions and stable gel formulations disclosed herein can also contain one or more excipients. Examples of excipients include but are not limited to pharmaceutically acceptable buffering agents, plasticizing agents, muco-adhesive agents, stabilizing agents, taste-masking agents, flavoring agents, breath freshening agents, coloring agents, antiseptic agents, inert filler agents, preserving agents, nonionic polymers, anionic polymers, softening agents, swelling agents, chelating agents, foaming agents, and combinations thereof. Examples of anionic polymers include but are not limited to poly(acrylic acid) and carboxymethycellulose.

In some aspects, the compositions or stable gel formulations disclosed herein can be formulated as buccal patch, buccal tablet or an intra-oral film.

In some aspects, the compositions and stable gel formulations disclosed herein can be used in combination with other therapeutic drugs used to treats subjects suffering from sialorrhea. For example, in some aspects, the compositions and stable gel formulations disclosed herein can be administered with glycopyrrolate. In some aspects, glycopyrrolate can be administered orally. In some aspects, the glycopyrrolate can be administered before, during or after the administration or application of any of the atropine compositions or stable gel formulations disclosed herein.

Methods of Treatment

Disclosed herein are methods of reducing the accumulation of saliva from the mouth of a subject. In some aspects, the methods can comprise applying intraorally a stable gel formulation comprising atropine in a pharmaceutically acceptable carrier to the subject. Also, disclosed herein are methods of treating sialorrhea in a subject. In some aspects, the methods can comprise applying intraorally a stable gel formulation comprising atropine in a pharmaceutically acceptable carrier to the subject. Further disclosed herein, are methods of treating or preventing sialorrhea in a subject, the method comprising: (a) identifying a subject in need of treatment; and (b) administering to the subject a therapeutically effective amount of a stable gel formulation comprising atropine disclosed herein.

In some aspects, the stable gel formulation can comprise atropine for intra-oral administration to the subject in an amount effective for decreasing saliva production in the subject.

In some aspects, the atropine can be atropine sulfate monohydrate. In some aspects, the atropine can be atropine sulfate. In some aspects, the atropine can be any salt form of atropine. In some aspects, the salt can be a pharmaceutically acceptable salt thereof. In some aspects, the atropine can be atropine sulfate anhydrous, atropine hydrochloride, atropine oxide, atropine oxide hydrochloride, atropine methylbromide, atropine borate, atropine nitrate, atropine tartrate, atropine citrate, atropine acetate, or atropine formate.

In some aspects, the atropine can be present in an amount up to about 0.01% to 1% by weight. In some aspects, the atropine can be present in an amount of 0.01%, 0.02%, 0.03%, 0.04%, 0.05%, 0.06%, 0.07%, 0.08%, 0.09%, 0.1% by weight or any amount in between.

In some aspects, the stable gel formulation can further comprise a polymer. In some aspects, the polymer can be a carbomer polymer. In some aspects, the carbomer polymer can be a carbomer 974P polymer. In some aspects, the carbomer 974P polymer can be present in amount up to about 0.5 to 5% by weight. In some aspects, the carbomer polymer can be present in amount up to about 0.5 to 5% by weight. In some aspects, the carbomer polymer can be present in amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between. In some aspects, the carbomer 974P polymer can be present in amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between. In some aspects, the carbomer polymer or carbomer 974P polymer can be any commercially available carbomer polymer or carbomer 974P polymer.

In some aspects, wherein the atropine can be present in amount up to about 0.1% by weight and the carbomer 974P polymer can be present in an amount up to about 5% by weight. In some aspects, the atropine can be present in amount of about 0.01%, 0.02%, 0.03%, 0.04%, 0.05%, 0.06%, 0.07%, 0.08%, 0.09%, 0.1% by weight or any amount in between and the carbomer 974P polymer can be present in an amount of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0% by weight or any amount in between.

In some aspects, the intra-orally administrable, compositions and stable gel formulation described herein can comprise atropine, or pharmaceutically acceptable salt thereof, per one dose in an amount ranging from 0.1 to 10 mg. In some aspects, the atropine, or pharmaceutically acceptable salt thereof can be present in the composition or stable gel formulation in amount of about 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, mg or any amount in between. In some aspects, the atropine, or pharmaceutically acceptable salt thereof can be present in the composition or stable gel formulation in a concentration range of between 25 to 300 µg/mL. In some aspects, the atropine, or pharmaceutically acceptable salt thereof can be present in the composition or stable gel formulation in a concentration range of 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 µg/mL or amount in between.

In some aspects, the formulation can have a dissolution rate of 1 to 6 hours. In some aspects, the formulation can have a dissolution rate of 30 minutes, 1 hour, 1.5 hours, 2, hours, 2.5 hours, 3 hours, 3.5 hours, 4 hours, 4.5 hours, 5 hours, 5.5 hours, 6 hours or any amount of time in between. In some aspects, the formulation can have a dissolution rate of 1, 2, 3, 4, 5, 10, 15, 20, 25, 30 minutes or any amount of time in between. In some aspects, the formulation can have a dissolution rate of 30, 35, 40, 45, 50, 55, 60 minutes or any amount of time in between. In some aspects, the stable gel formulation of atropine is intraorally applied every 6 hours.

In some aspects, the subject can have a neurodevelopment disorder. In some aspects, the neurodevelopment disorder can be cerebral palsy or dystonia. In some aspects, the subject can have Parkinson's disease, cerebral palsy, motor neuron disease, acquired brain injury or stroke. In some aspects, the subject can have drooling or excess saliva production in the mouth or aialorrhea caused by one or more of the following drugs: clozapine, risperidone, nitrazepam, lithium, and bethanechol. In some aspects, the subject can have Wilson's disease, Angelman syndrome, idiopathic paroxysmal sialorrhea or heavy metal poisoning. In some aspects, the subject can have an infection. In some aspects, the subject can have pharyngitis or tonsillitis. In some aspects, the pharyngitis or tonsillitis can be caused by an infection. In some aspects, the subject can be terminally ill.

In some aspects, the subject can be identified in need of treatment prior to the application of a composition or stable gel formulation described herein.

The compositions and stable gel formulations described herein can be formulated to include a therapeutically effective amount of atropine. In some aspects, atropine can be contained within a pharmaceutical formulation. In some aspects, the pharmaceutical formulation can be a unit dosage formulation. In some aspects, atropine or any of the compositions and formulations described herein can be administered on an as-needed basis.

Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to sialorrhea or increased saliva production.

The pharmaceutical compositions described herein can be administered to the subject (e.g., a human patient) in an amount sufficient to delay, reduce, prevent or reverse the onset or duration of sialorrhea or increased saliva production in a subject. Accordingly, in some aspects, the patient can be a human patient. In therapeutic applications, compositions and formulations described herein can be administered to a subject (e.g., a human patient) already expressing or diagnosed with sialorrhea or increased saliva production in an amount sufficient to at least partially improve sialorrhea or increased saliva production or arrest sialorrhea or increased saliva production, its complications, and consequences. An amount adequate to accomplish this is defined as a therapeutically effective amount. A therapeutically effective amount of a pharmaceutical composition can be an amount that achieves a cure or reverses sialorrhea or increased saliva production, but that outcome is only one among several that can be achieved. As noted, a therapeutically effect amount includes amounts that provide a treatment in which the onset, progression or expression of one or more of the side effects associated with sialorrhea or increased saliva production can be delayed, hindered, or prevented, or the one or more symptoms associated with sialorrhea or increased saliva production can be reduced, ameliorated or reversed. One or more of the symptoms can be less severe. Recovery can be accelerated in an individual who has been treated. In some aspects, the one or more side effects associated with sialorrhea or increased saliva production include but are not limited to perioral chapping, dehydration, odor and social stigmatization.

Amounts effective for this use can depend on the severity of the sialorrhea or increased saliva production and the weight and general state and health of the subject, but generally range from about 25 to 300 µg/mL of an equivalent amount of the atropine per dose per subject.

The total effective amount of a atropine as disclosed herein can be administered to a subject as a single dose, either as a bolus or by infusion over a relatively short period of time, or can be administered using a fractionated treatment protocol in which multiple doses are administered over a more prolonged period of time.

The therapeutically effective amount or dosage of the atropine used in the methods as disclosed herein applied to mammals (e.g., humans) can be determined by one of ordinary skill in the art with consideration of individual differences in age, weight, sex, other drugs administered and the judgment of the attending clinician. Variations in the needed dosage may be expected. Variations in dosage levels can be adjusted using standard empirical routes for optimization. The particular dosage of a pharmaceutical composition to be administered to the patient will depend on a variety of considerations (e.g., the severity of side effects of sialorrhea or the sialorrhea condition itself), the age and physical characteristics of the subject and other considerations known to those of ordinary skill in the art.

Pharmaceutical Compositions

Disclosed herein are pharmaceutical compositions, comprising atropine and a pharmaceutical acceptable carrier described herein. Disclosed herein are pharmaceutical compositions, comprising a stable gel formulation of atropine and a pharmaceutical acceptable carrier. In some aspects, atropine can be formulated for intra-oral administration. The compositions or stable gel formulations can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The compositions and stable gel formulations disclosed herein can be administered directly to a subject. Generally, the compositions can be suspended in a pharmaceutically acceptable carrier (e.g., physiological saline or a buffered saline solution) to facilitate their delivery.

The compositions and stable gel formulations disclosed herein can be formulated in various ways for intra-oral administration. Where suitable, oral formulations can take the form of a gel, which may be enterically coated or otherwise protected. Sustained release formulations can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for intra-oral administration. Thus, compositions can be prepared for intra-oral administration that includes atropine dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions are formulated for application to a mucosal surface, one or more of the excipients can be a solvent or emulsifier for the formulation of a gel, and the like.

The pharmaceutical compositions can be sterile and sterilized by conventional sterilization techniques or sterile filtered. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tubes.

Articles of Manufacture

The compositions and stable gel formulations described herein can be packaged in a suitable container labeled, for example, for use as a therapy to reduce accumulation of saliva in the mouth or treat sialorrhea in a subject. Accordingly, packaged products (e.g., sterile containers containing the composition or stable gel formulations described herein and packaged for storage, shipment, or sale at concentrated or ready-to-use concentrations) and kits, including at least atropine as described herein and instructions for use, are also within the scope of the disclosure. A product can include a container (e.g., a vial, jar, bottle, bag, or the like) containing the composition or stable gel formulations described herein. In addition, an article of manufacture further may include, for example, packaging materials, instructions for use, dosing cards for measuring the dose and/or applicators for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the composition or stable gel formulations therein should be administered (e.g., the frequency and route of administration), indications therefor, and other uses. The composition or stable gel formulations can be ready for administration (e.g., present in dose-appropriate units), and may include a pharmaceutically acceptable adjuvant, carrier or other diluent. Alternatively, the composition or stable gel formulations can be provided in a concentrated form with a diluent and instructions for dilution.

A variety of containers and packaging can be used for the intra-oral administration of atropine in a stable gel formulation described herein, including but not limited to single-use, tubes, and the like. In some aspects, the containers and packages can have an easy-opening design.

Disclosed herein are kits comprising the composition or stable gel formulations described herein, wherein the composition or gel formulation is in a plastic tube. In some aspects, the kits can further comprise a dosing card for measuring the dose. In some aspects, the dosing card can be made of a plastic material. In some aspects, the kid can also comprise an applicator.

EXAMPLES

Example 1: Formulation, Characterization and Batch Stability of 0.01% Atropine Gel Preparation of atropine gel (0.01%). One gram of Carbopol 974 will be added to 100 mL sterile water for injection USP and mixed until the polymer is homogeneously dispersed. To this mixture, 10 mg of atropine sulfate powder will be added and mixed until atropine sulfate is completely dissolved. Finally, a 20 wt % NaOH solution was added dropwise to adjust the pH of the gel to 7.0. The water concentration will be adjusted based on the amount of NaOH solution added. The clear gel formed will be mixed for an additional 15 minutes for homogeneity. The final gel will be dispensed in an ointment jar with a 1 gram measuring spoon. Table 1 shows the quantitative composition of each component of the atropine gel (0.01%).

TABLE 1

Components of composition.

| Ingredient Listing | Quantity |
|---|---|
| Atropine sulfate monohydrate USP | 10 mg |
| Carbopol 974 NF | 1 gram |
| Sterile Water for Injection, USP | Up to 100 mL |
| 20% Sodium Hydroxide Solution | 2 to 3 drops |

Figure 1B:
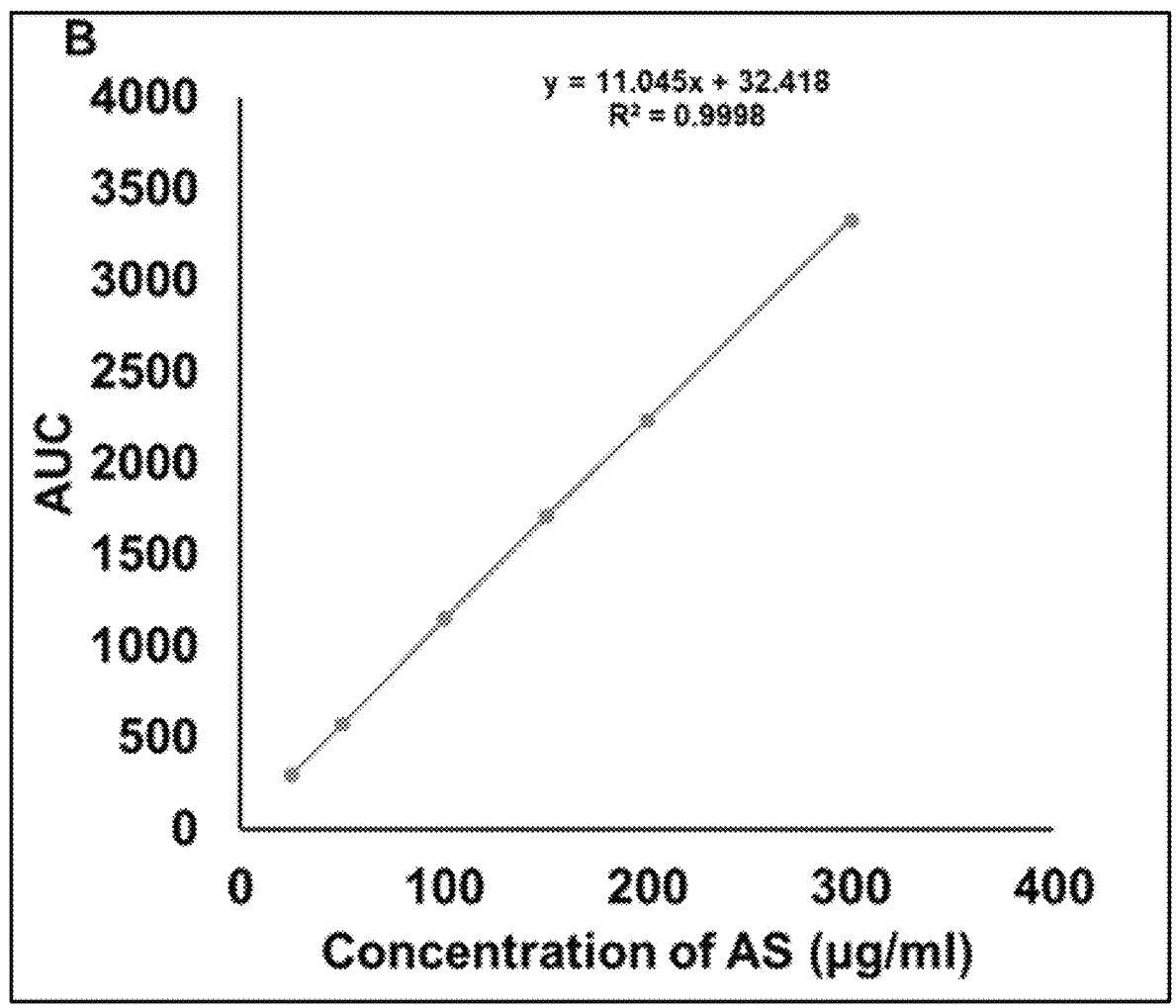

Development and validation of a high-performance liquid chromatography (HPLC) method for quantification of atropine in the gel formulation. The HPLC separations were carried out on a C18, Gemini® NX column (5 μm i.d; 4.6×150 mm) with phosphate buffer: acetonitrile (60:40); pH 4.00 as a mobile phase on an Agilent HPLC. The atropine was detected at a wavelength of 220 nm using an Agilent Photo Diode Array detector. FIG. 1A shows a representative atropine chromatogram, and FIG. 1B shows the linearity of the atropine standard within a concentration range of 25 to 300 μg/mL. The HPLC method was validated for accuracy and precision according to FDA guidelines for method validation, and the values were within FDA specific limits.

Figure 2:
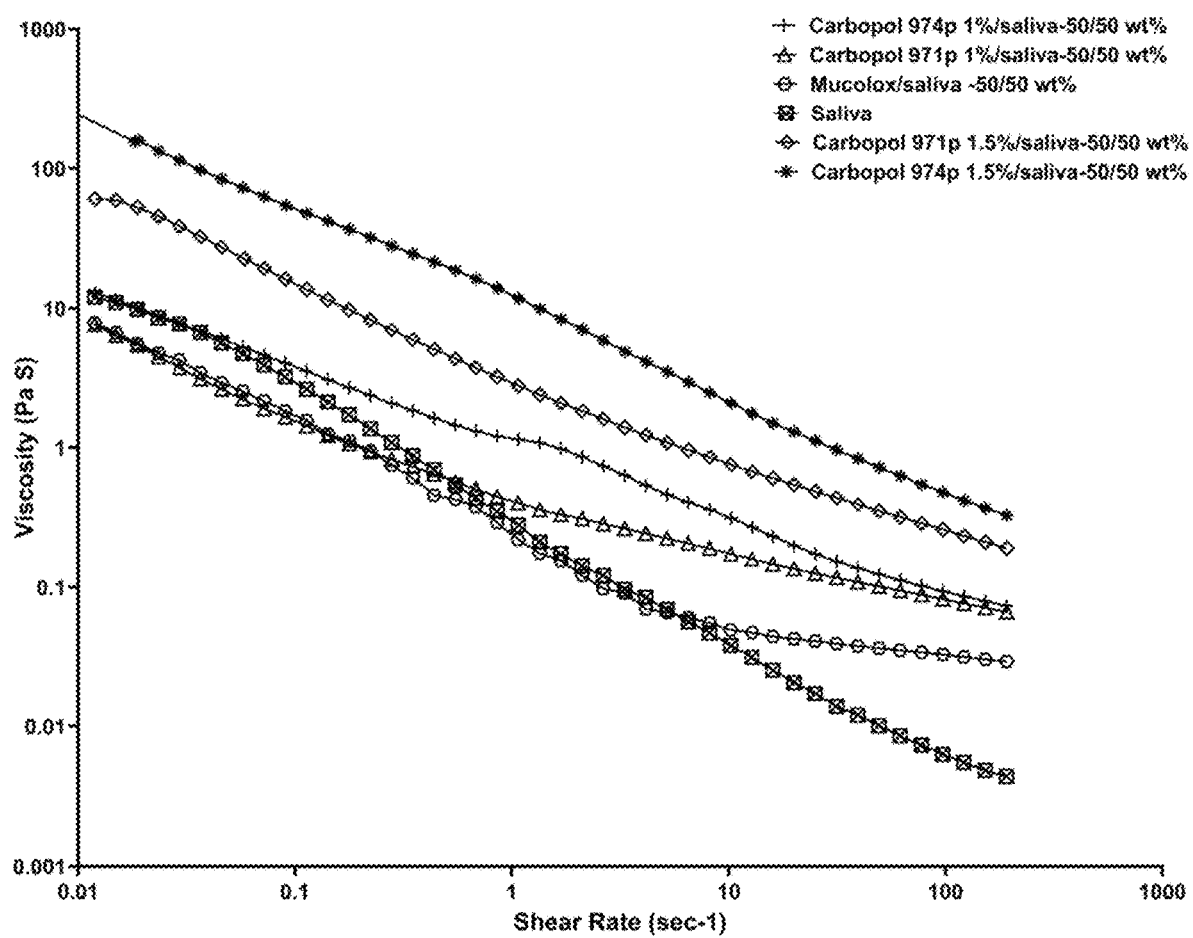
FIG. 2 shows the viscosities of oral gel/saliva mixture at different shear rates.

Evaluation of the mucoadhesiveness of different oral gel formulations using rheology. Pooled saliva samples collected from pediatric patients were mixed with an equal volume of oral gel formulations, and the viscosity was measured using a Kinexus ultra+®, Malvern Analytical, USA rheometer. FIG. 2 shows the viscosity of saliva and oral gel formulation mixtures. Compared to saliva, the saliva/Mucolox® mixture showed a reduced viscosity at lower shear rates, and the viscosity plateaus at higher shear rates. Saliva mixtures with Carbopol® 971 (1%), Carbopol® 971 (1.5%), Carpobol® 974 (1%) and Carpobol® 974 (1.5%) showed an increase in viscosity compared to saliva. These results show that there are more interactions between these polymers and saliva compared to saliva and mucolox. Thus, Carbopol® 971 and Carbopol® 974 act as better mucoadhesive polymers compared to Mucolox®, a mucoadhesive polymer.

Figure 3:
FIG. 3 shows the in vitro release apparatus.
Figure 4:
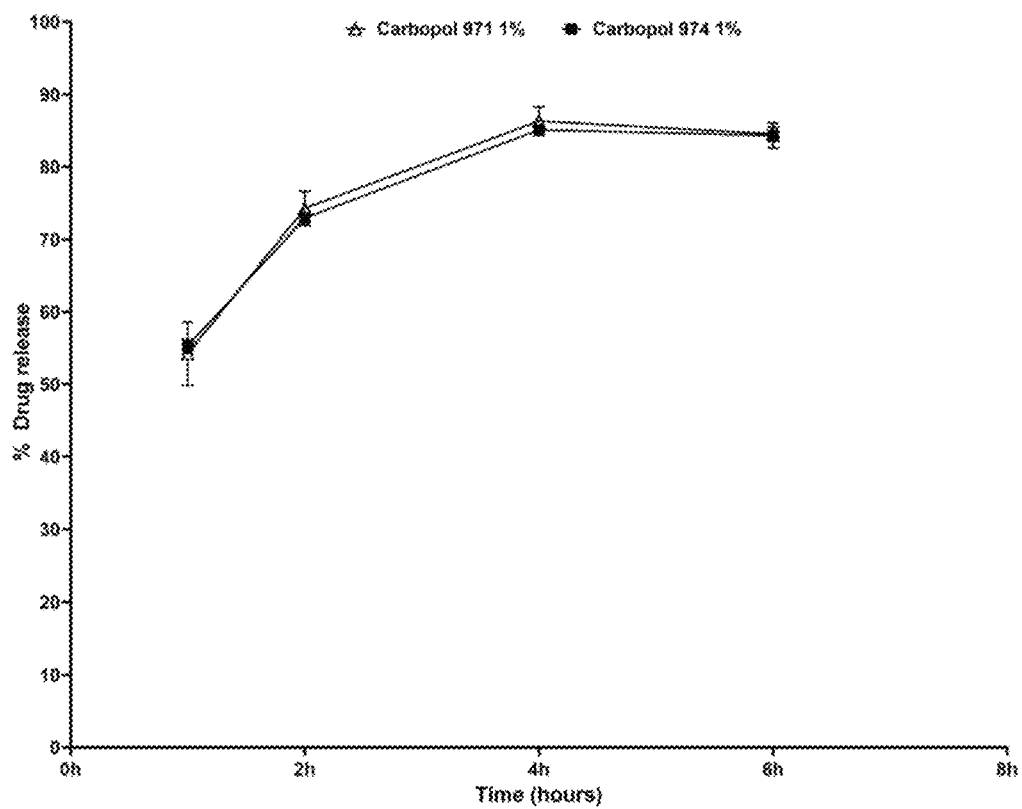
FIG. 4 shows in vitro release of atropine from gels.

In vitro release of atropine from the gel formulation. The in vitro release of atropine form the atropine gel formulations prepared using Carbopol® 971 and Carbopol® 974 was performed using the dialysis membrane technique. Briefly, 1 gm of atropine gel was transferred into dialysis membrane tubing, placed in 40 ml of phosphate buffer in a 50 mL centrifuge tube, and placed in an incubator at 37° C. and 50 rpm. FIG. 3 shows the apparatus for in vitro release. A one mL aliquot of sample was collected at each time point, and the atropine released was analyzed using HPLC. FIG. 4 shows the release profile of various atropine gel formulations. The results show that approximately 85% of atropine is released from the gel by 6 hours.

Batch analysis for quality control of atropine gel formulation. The physical and chemical stability of atropine gel formulation prepared with Carbopol® 974 was evaluated at room temperature and under refrigeration for a period of 30 days. The microbiological stability of atropine gel formulation was evaluated for a period of 30 days using USP <61>: Microbiological examination of nonsterile products: Microbial enumeration tests. For each batch, twenty atropine gel formulations were prepared as described herein and stored at either room temperature or in the refrigerator. At 0, 14, and 30 days, three containers of atropine gels were randomly selected, and their physical, chemical, and microbiological stability was assessed by appropriate methods. Table2 shows the final results of the tests. Details about each individual test is provided herein. These data demonstrate that the atropine gel is physically and chemically stable at room temperature and under refrigerated conditions for up to one week and is microbiologically stable for up to 30 days. This experiment also confirms the batch stability of the atropine gels.

TABLE 2

Batch analysis for quality control of atropine gel formulation

| Quality Test | Method | Result |
| --- | --- | --- |
| Clarity | Visual inspection against dark and light background | Passed<br>The atropine gel formulation (0.01%) did not show any precipitates of aggregates |
| Microbial Enumeration Test | USP61 | Passed<br>No growth was observed in the samples for up to 30 days of testing when samples were stored at room temperature. |
| Stability of atropine in atropine gel formulation | Validated stability-using HPLC | Passed<br>The assay of atropine for the samples tested was between 90 to 110%. |

Clarity. The clarity of 0.01% atropine gel was evaluated at 0 hours and at a 7 day time point using dark and light backgrounds. At both time points, the 0.01% atropine gel was clear without any visible particles, aggregates, or precipitates.

Microbial Enumeration Test (USP 61). The microbial enumeration test (USP 61) of 0.01% atropine gel was performed by the Compounder's International Analytical Laboratory, Castle Rock, Co, USA. The samples after preparation were stored at room temperature for 0, 14, and 30 days, and then the microbial enumeration tests were performed. The microbial enumeration tests were performed according to the method outlined in the United States Pharmacopeia (USP) 61: Microbiological examination of nonsterile products: Microbial enumeration tests. The results show that no microbial growth was observed in any of the three samples of 0.01% atropine gel tested. A Certificate of Analysis was received. Chemical stability of atropine in atropine gel formulation. The chemical stability of atropine in 0.01% atropine gel was evaluated after storing the gel at room temperature and at 4° C. for 7 days. Stability using an HPLC assay for the determination of amiloride content was developed and validated according to Food and Drug Administration guidelines for bioanalytical method validation. The amount of atropine in the 0.01% atropine gel was calculated based on a calibration curve prepared from various concentrations of Atropine Monohydrate Reference Standard. The HPLC method described herein was used for the quantification of atropine. The data from the chemical stability tests showed that atropine in 0.01% atropine gel was stable for 7 days when stored at room temperature and at 4° C. Table 3 shows the % of atropine in 0.01% atropine gel at 0, 24 hours, 7 days, 14 days, and 30 days.

TABLE 3

Percent of atropine in 0.01% atropine gel after storing at room temperature and refrigeration for up to 7 days.

| | % Atropine* | | | | |
| --- | --- | --- | --- | --- | --- |
| Storage Condition | 0 hours | 24 hours | 7 days | 14 Days | 30 Days |
| Room Temperature (25-27° C.) | 97.2 ± 2.1 | 99.1 ± 3.2 | 97.6 ± 2.8 | 108.6 ± 2.4 | 90.2 ± 1.8 |
| Refrigerated (4-8° C.) | 97.2 ± 2.1 | 97.6 ± 2.6 | 98.1 ± 3.2 | 100.1 ± 2.1 | 94.0 ± 1.1 |

*Each value is an average of three runs with standard deviation.

Example 2: Single-Dose Pharmacokinetics of Atropine Oral Gel in Healthy Adults Described herein is the development of a mucoadhesive atropine-gel for the treatment of pediatric sialorrhea. The single-dose pharmacokinetics of atropine oral gel will be evaluated in healthy adults. The data obtained from this study will inform the understanding of the pharmacokinetics of atropine after oro-transmucosal administration providing a dose versus plasma concentration relationship.

The development of a mucoadhesive gel formulation of atropine can be designed for the treatment of pediatric sialorrhea. The pharmacokinetics of atropine in adults after topical oral administration will help guide administration and treatment regimens and protocols in adults and children. Because of the mucoadhesive property of the polymer Carbopol®, atropine will retain in the oral cavity for a prolonged period reducing the need for frequent administration (Singla A K, Chawla M, Singh A 2000. Drug Dev Ind Pharm, 26(9):913-924; Keegan G, et al. 2007. Int J Pharm, 340(1-2):92-96; and Kelly H M, et al. 2004. Int J Pharm 278(2):391-406. The mucoadhesive property of Carbopol® towards oral mucosa was proven clinically in a multi-institutional, randomized, double-blind, placebo-controlled trial (Allison R R, et al. 2014. Cancer, 120(9):1433-1440). The systemic absorption of atropine will also reduce due to its affinity towards Carbopol® rather than oral mucosa resulting in fewer systemic side effects. The mucoadhesive gel formulation will also avoid medication errors that are associated with off-label use of atropine eye drops. The data generated will shift the treatment strategy for pediatric sialorrhea from off-label medication use to a standardized treatment with a well-characterized dosage form and established dosage regimen.

Described herein is a formulation combining an FDA-approved mucoadhesive polymer Carbopol® 974 NF and atropine, an FDA-approved drug currently used clinically. Specifically, in pediatrics, Carbopol® is used as lubricant eye drops for the treatment of dry eyes (Alcon (2018). Viscotears® Liquid Gel [carbomer (polyacrylic acid)]—Patient Information Leaflet). Carbopol® 974 NF is recognized by the FDA as Generally Regarded as Safe (GRAS). The single-step formulation approach for the preparation of mucoadhesive atropine gel can be easily scaled-up for broader clinical investigations. Also provided herein is an evaluation of the clinical efficacy of mucoadhesive atropine gel in pediatric sialorrhea patients.

The methods will assess the detectable concentrations of atropine in plasma following topical oral administration in gel formulation, allowing the evaluation of pharmacokinetics in healthy adults.

The methods described herein can evaluate single-dose pharmacokinetics of atropine gel (0.01% w/w) at 0.1 mg atropine dose in healthy adults; and calculate the following pharmacokinetic parameters after topical oral administration of atropine gel: time to reach maximum plasma concentration (Tmax), maximum plasma concentration (Cmax), area under the curve (AUC), the volume of distribution (Vd) and clearance (CL).

Atropine Sulfate. Atropine, a cholinergic muscarinic antagonist, occurs as white crystals, usually needle-like, or as a white, crystalline powder. It is highly soluble in water with a molecular weight of 289.38. Atropine, a *belladonna* alkaloid, is a racemic mixture of equal parts of d- and l-hyoscyamine; its activity is due almost entirely to the levo isomer of the drug.

Chemically, atropine is designated as 1αH,5αH-tropan-3-ol (±)-tropate (ester). It's empirical formula is $C_{17}H_{23}NO_3$, and its structural formula is:

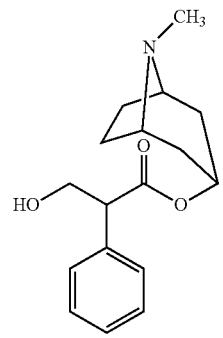 [SMILES: CN1C2CCC1CC(OC(=O)C(CO)c1ccccc1)C2]

Mechanism of Action. Atropine competitively blocks the effects of acetylcholine, including excess acetylcholine due to organophosphorus poisoning, at muscarinic cholinergic receptors on smooth muscle, cardiac muscle, secretory gland cells, and in peripheral autonomic ganglia and the central nervous system.

Pharmacodynamics. Atropine reduces secretions in the mouth and respiratory passages, relieves the constriction and spasm of the respiratory passages, and may reduce the paralysis of respiration that results from toxic nerve agents, which increase anticholinesterase activity in the central nervous system. Atropine-induced parasympathetic inhibition may be preceded by a transient phase of stimulation, especially on the heart where small doses first slow the rate before characteristic tachycardia develops because of paralysis of vagal control. Although mild vagal excitation occurs, the increased respiratory rate and occasionally increased depth of respiration produced by atropine are more likely the result of bronchiolar dilatation. Accordingly, atropine is an unreliable respiratory stimulant, and large or repeated doses may depress respiration.

Adequate doses of atropine can prevent or abolish various types of reflex vagal cardiac slowing or asystole. The drug also can prevent or abolish bradycardia or asystole produced by injection of choline esters, anticholinesterase agents or other parasympathomimetic drugs, and cardiac arrest produced by stimulation of the vagus. Atropine may also lessen the degree of partial heart block when vagal activity is an etiologic factor. In some individuals with complete heart block, the idioventricular rate may be accelerated by atropine; in others, the rate is stabilized. In some patients with conduction defects, atropine may cause paradoxical atrio-ventricular (A-V) block and nodal rhythm.

Systemic doses of atropine slightly raise systolic and lower diastolic pressures and can produce significant postural hypotension. Such doses also slightly increase cardiac output and decrease central venous pressure. Atropine can dilate cutaneous blood vessels, particularly in the "blush" area (atropine flush), and may cause overheating due to suppression of sweat gland activity.

Pharmacokinetics. There are no reports of the pharmacokinetics of atropine after topical oral administration. Atropine is well absorbed after intramuscular administration. Atropine is distributed throughout the various body tissues and fluids. Much of the drug is metabolized by enzymatic hydrolysis, particularly in the liver; from 13 to 50% is excreted unchanged in the urine. The approximate peak plasma concentration Cmax of atropine following 1.67 mg atropine given intramuscularly to adults by the 2 mg AtroPen® delivery system was 9.6±1.5 (mean±SEM) ng/mL. The mean time to maximum plasma concentration (Tmax) was 3 minutes. The plasma half-life T½ of intravenous atropine in pediatric subjects over 2 years is 2.5±1.2 (mean±SD) hours; in adults 16-58 years, the T½ is 3.0±0.9 (mean±SD) hours; in geriatric patients 65-75 years it is 10.0±7.3 (mean±SD) hours. The protein binding of atropine is 14 to 22% in plasma. There are gender differences in the pharmacokinetics of atropine. The AUC (0-inf) and Cmax were 15% higher in females than males. The half-life of atropine is slightly shorter (approximately 20 minutes) in females than males.

In a study of healthy subjects, after topical ocular administration of 30 μL of atropine sulfate ophthalmic solution, 1%, the mean (±SD) systemic bioavailability of 1-hyoscyamine was reported to be approximately 64±29% (range 19% to 95%) as compared to intravenous administration of atropine sulfate. The mean (±SD) Tmax was approximately 28±27 minutes (range 3 to 60 minutes), and the mean (±SD) Cmax of 1-hyoscyamine was 288±73 pg/mL. The mean (±SD) plasma half-life was reported to be approximately 2.5±0.8 hours. In a separate study of patients undergoing ocular surgery, after topical ocular administration of 40 μL of atropine sulfate ophthalmic solution, 1%, the mean (±SD) plasma Cmax of 1-hyoscyamine was 860±402 pg/mL.

Systemic Adverse Reactions. Systemic effects of atropine are related to its anti-muscarinic activity. Systemic adverse events reported include dryness of skin, mouth, and throat from decreased secretions from mucus membranes; blurred vision, dry eyes, photophobia, urinary hesitance or retention, constipation, abdominal pain, abdominal distension, drowsiness; restlessness, irritability or delirium from stimulation of the central nervous system; tachycardia; flushed skin of the face and neck.

Study Design. Described herein is a single-dose, single-center, open-label study of the pharmacokinetics of atropine gel (0.01% w/w) after topical oral administration in healthy adults. Each of the study participants will receive 1 gram of atropine gel (0.01% w/w) containing 0.1 mg atropine via self-administration of gel into the oral cavity. A series of timed blood samples (0, 5, 10, 15, 30, 60 minutes, and 2, 4, 6, 8, and 24 hours, 7 mL each time point) will be collected in commercial tubes, and plasma will be separated by centrifugation. The plasma samples will be stored frozen until further analysis.

On day one, cardiac function will be monitored using EKG if tachycardia (Heart rate>90 beats per minute) is observed. Blood samples will be obtained via placement of an IV catheter. Catheter will be removed at the end of first day and 24 hour blood sample will be an additional stick.

At 24 hour time-point, systemic adverse events of atropine such as urinary retention, palpitations, tachycardia, blurred vision, restlessness, tremor, constipation, drowsiness, etc. will be evaluated. Twenty-four hour blood draw will be performed. Blood samples will be processed and plasma will be analyzed for atropine content using LC-MS/MS. The pharmacokinetic analyses will be performed on plasma concentration versus time data using non-compartmental analysis.

Heart rate will be measured every hour for up to 8 hours and vital signs will be measured at 0, 2, 4, 6, 8, and 24 hour time points EKG will be performed if tachycardia (Heart Rate>90 bpm) is observed. After an 8-hour time point, vital signs, heart rate and blood pressure will be measured.

The usual adult dose of atropine after intravenous, subcutaneous, or intramuscular administration is between 0.5 mg to 3 mg depending on the indication with a maximum total dose of 3 mg (Atropine sulfate injection. Full Prescribing Information. accessdata.fda.gov/drugsatfda_docs/label/2015/021146s0151bl.pdf). As disclosed herein, 0.1 mg of atropine will be administered by topical oral route which is 30 times lower than the maximum total dose of atropine administered by IV/SC/IM routes.

Pharmacokinetic Sample Collection. A total of 11 blood samples will be collected from each subject for pharmacokinetic analysis. Blood (7 mL) will be collected in commercial tubes with appropriate anticoagulant via venipuncture at 0 mins (pre-dose), 5 min, 10 min, 15 min, 30 min, 60 min, 2 h, 4 h, 6 h, 8 h, and 24 h post-dose. The predose sample will be taken up to 90 minutes prior to dosing.

The time and date of collection for each sample will be recorded. Collected blood samples will be centrifuged for 15 minutes at 3400 rpm at 4° C. The plasma from each tube will be split and approximately half transferred to each of two labeled polypropylene screw-cap tubes and frozen at −20° C. The samples will remain frozen until assayed.

Pharmacokinetic analysis. A standard non-compartmental approach will be applied for the pharmacokinetic analysis of the atropine plasma concentration versus time data from the study. The pharmacokinetic parameters area under the plasma concentration versus time curve from 0 to the last time point t measured AUC0-t, Area under the plasma concentration versus time curve from 0 to infinity, AUC0-∞, maximum concentration (Cmax), time to reach maximum concentration (Tmax), half-life (t½), and terminal elimination rate constant, Kel will be calculated using Phoenix® Winnonlin®. For calculation of AUC0-t and AUC0-∞, a concentration of zero will be assigned to each sample at time=0 (pre-dose). Pharmacokinetic parameters will be generated using Phoenix® Winnonlin® program.

Example 3: Evaluation of Viscosity and Mucoadhesive Properties of Carbopol

An important product characteristic of an oral gel can be to have the appropriate viscosity and mucoadhesion so that the gel can be easily squeezed from the tube and applied to the oral mucosa and resides in the oral cavity for an extended period. Therefore, the viscosity and mucoadhesive properties of Carbopol 974 were compared with other widely used mucoadhesive polymers Carbopol 971, Poloxamer, and Mucolox. Mucolox is a mucoadhesive polymer used by compounding pharmacies across the United States to prepare oral gels. Mucolox is also widely used as a compounding base for dental, wound, rectal, and vaginal gels. Carbopol 971 and poloxamer are widely used polymers in several commercially available oral gels. The viscosity and mucoadhesive properties of Carbopol were also evaluated at the concentration range of 0.5 to 1.5%.

Figure 5:
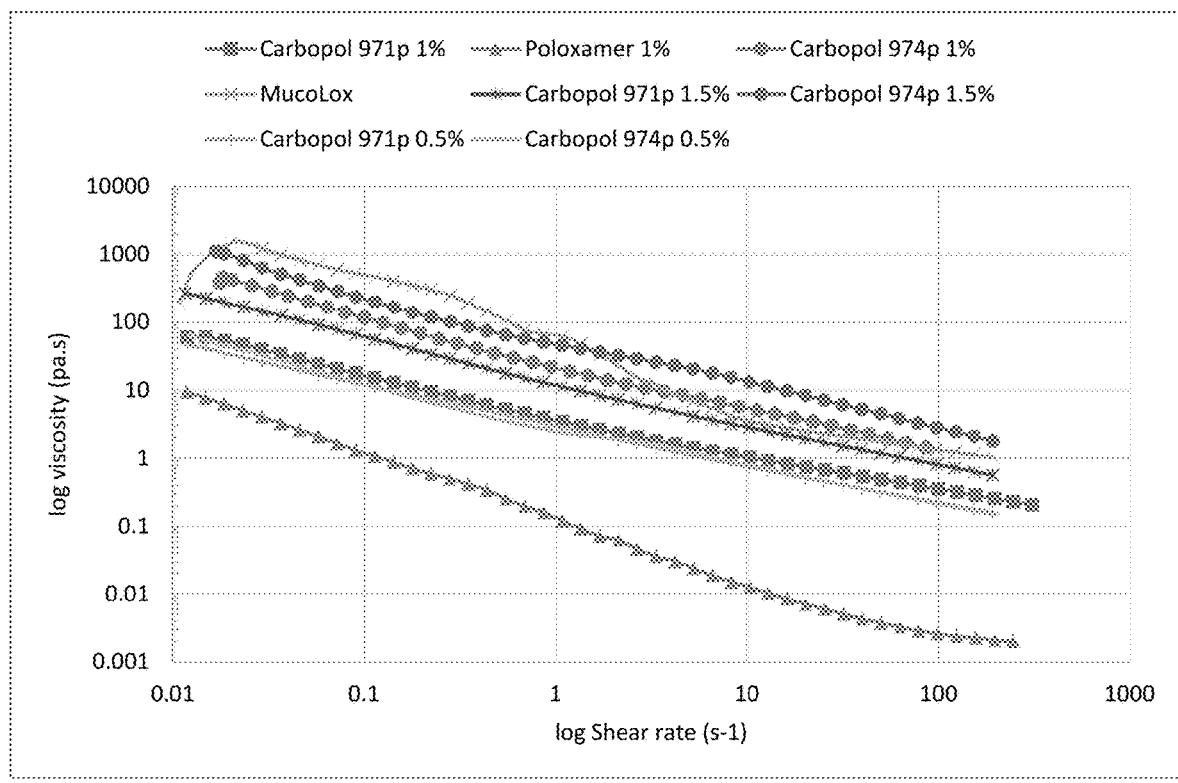
FIG. 5 shows the viscosities of oral gels prepared using various polymers.
Figure 6:
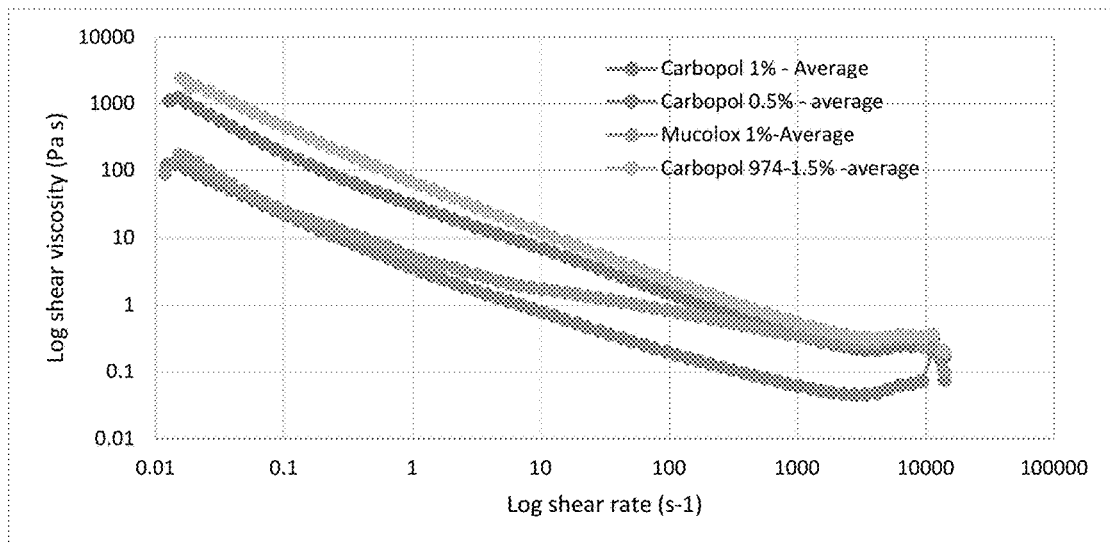
FIG. 6 shows viscosities of the oral gel prepared using various concentrations of carbopol.

The viscosity of the formulations containing polymers at different concentrations was tested to evaluate the spreadability characteristic of the gel, which is an important quality attribute of oral gel. The mucoadhesive property of the gel was tested by mixing the gels made with various polymers with human saliva. Mucolox was used as a standard to compare the viscosity and mucoadhesion properties. The viscosity of Carbopol 974p at 1.0% and 1.5%, and Carbopol 971p at 1.5% were higher and linear with respect to increasing shear rate when compared to the viscosity of mucolox (FIGS. 5 and 6). These data demonstrate that carbopol polymers are more suitable for the gel formulation described herein when compared to mucolox, and will result in an oral gel composition with better spreadability than mucolox.

Furthermore, the results demonstrated that Carbopol 974 has better viscosity compared to Carbopol 971 resulting in the use of Carbopol 974 for an oral gel composition as described herein (FIG. 5).

Figure 7:
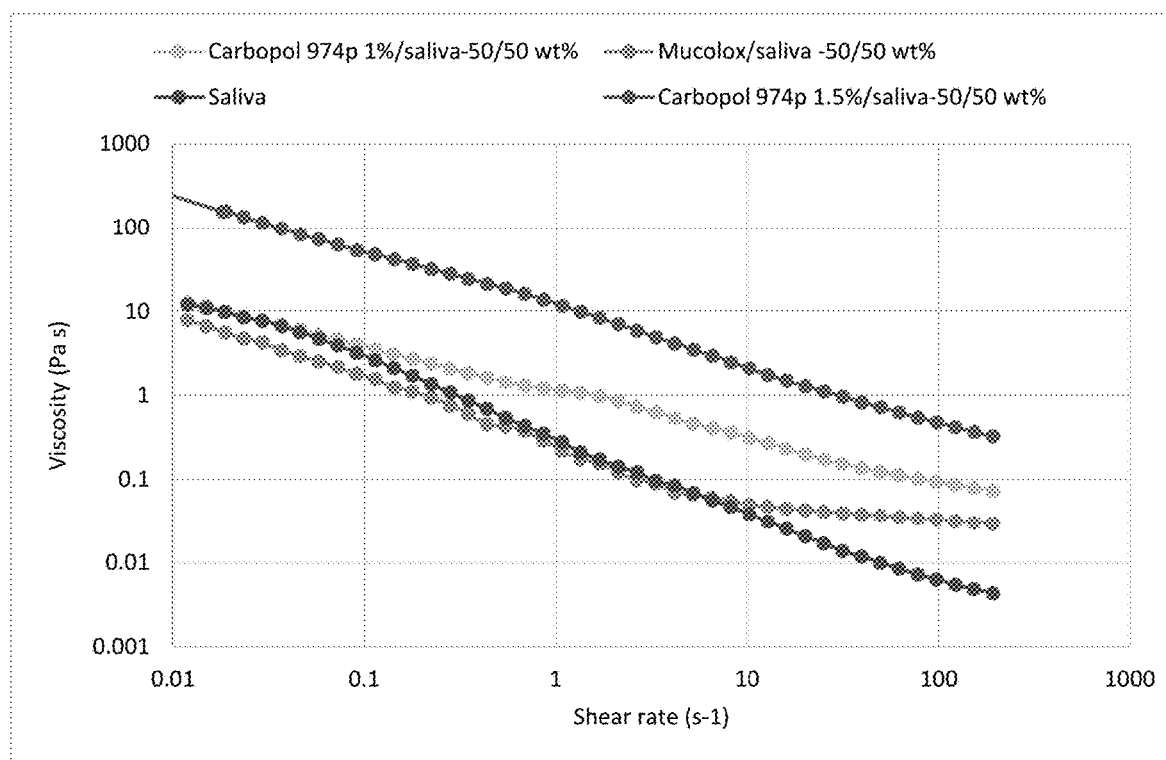
FIG. 7 shows the comparison of mucoadhesive properties of oral gels prepared from carbopol and mucolox. The mucoadhesive property was measured by evaluating the change in viscosity of the gel after mixing with human saliva.

When mixed with saliva the viscosity of mucolox was comparable with the viscosity of saliva indicating that mucolox can be easily detached from the mucin in saliva and can get washed away easily. These data further strengthen the use of Carbopol in the gel formulation described herein. Carbopol 974p 1.5% and 1.0% showed higher viscosity than saliva indicating that Carbopol 974p 1.5% and 1.0% may stay in the oral cavity for a longer period (FIG. 7).

Although, Carbopol 974p 1.5% had higher viscosity than Carbopol 974p 1.0%, the formulation containing Carbopol 974p 1.5% had more bubbles and did not form a clear gel which is an important organoleptic characteristic for a gel formulation and also may affect the homogeneity of the formulation. Thus, Carbopol 974 1.0% was used.

What is claimed is:

1. A stable gel formulation comprising atropine sulfate monohydrate and carbomer 974P polymer for intraoral administration of the atropine sulfate monohydrate to a subject in an amount effective for decreasing saliva production in the subject.

2. The stable gel formulation of claim 1, wherein the atropine sulfate monohydrate is present in an amount of 0.01% to 1% by weight.

3. The stable gel formulation of claim 1, wherein the carbomer 974P polymer is present in an amount of 0.5 to 5% by weight.

4. The stable gel formulation of claim 3, wherein the atropine sulfate monohydrate is present in an amount of 0.1% by weight and the carbomer 974P polymer is present in an amount of 5% by weight.

5. The stable gel formulation of claim 4, wherein the formulation has a dissolution time of 1 to 6 hours.

6. The stable gel formulation of claim 1, wherein the atropine sulfate monohydrate is present in the formulation in a concentration range of between 25 to 300 μg/mL.

7. The stable gel formulation of claim 1, wherein the formulation further comprises an excipient selected from the group consisting of a pharmaceutically acceptable buffering agent, a plasticizing agent, a muco-adhesive agent, a stabilizing agent, a taste-masking agent, a flavoring agent, a breath freshening agent, a coloring agent, an antiseptic agent, an inert filler agent, a preserving agent, nonionic polymer, anionic polymer, softening agent, swelling agent, chelating agent, foaming agent, and combinations thereof.

8. A method of reducing the accumulation of saliva from the mouth of a subject, the method comprising applying intraorally a stable gel formulation of atropine sulfate monohydrate in a pharmaceutically acceptable carrier to the subject, wherein the pharmaceutically acceptable carrier is a carbomer 974P polymer.

9. A method of treating sialorrhea in a subject, the method comprising applying intraorally a stable gel formulation of atropine sulfate monohydrate in a pharmaceutically acceptable carrier to the subject, wherein the pharmaceutically acceptable carrier is a carbomer 974P polymer.

10. The method of claim 9, wherein the subject has Parkinson's disease, cerebral palsy, motor neuron disease, acquired brain injury, dementia, or stroke.

11. The method of claim 9, wherein the stable gel formulation comprises atropine sulfate monohydrate for intraoral administration to the subject in an amount effective for decreasing saliva production in the subject.

12. The method of claim 9, wherein the atropine sulfate monohydrate is present in an amount of 0.01% by weight.

13. The method of claim 9, wherein the carbomer 974P polymer is present in an amount of 0.5 to 5% by weight.

14. The method of claim 13, wherein the atropine sulfate monohydrate is present in an amount of 0.1% by weight and the carbomer 974P polymer is present in an amount of 5% by weight.

15. The method of claim 14, wherein the formulation has a dissolution time of 1 to 6 hours.

16. The method of claim 8, wherein the stable gel formulation of atropine is intraorally applied every 6 hours.

* * * * *